United States Patent
Kim et al.

(10) Patent No.: US 7,642,369 B2
(45) Date of Patent: Jan. 5, 2010

(54) EPOXYKETONE-BASED IMMUNOPROTEASOME INHIBITORS

(75) Inventors: Kyung Bo Kim, Lexington, KY (US); Yik Khuan Ho, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 605 days.

(21) Appl. No.: 11/531,129

(22) Filed: Sep. 12, 2006

(65) Prior Publication Data

US 2008/0064659 A1    Mar. 13, 2008

(51) Int. Cl.
*C07C 269/00* (2006.01)
(52) U.S. Cl. .................... 560/24; 549/416; 549/513
(58) Field of Classification Search ........... 549/416, 549/513; 560/24
See application file for complete search history.

(56) References Cited

U.S. PATENT DOCUMENTS

| | | | |
|---|---|---|---|
| 3,062,841 | A | 11/1962 | Yang et al. |
| 4,990,448 | A | 2/1991 | Konishi et al. |
| 5,071,957 | A | 12/1991 | Konishi et al. |
| 6,831,099 | B1 | 12/2004 | Crews et al. |
| 2004/0266664 | A1 | 12/2004 | Crews et al. |
| 2005/0101781 | A1 | 5/2005 | Agoulnik et al. |
| 2005/0245435 | A1 | 11/2005 | Smyth et al. |
| 2006/0030533 | A1 | 2/2006 | Smyth et al. |
| 2006/0088471 | A1 | 4/2006 | Bennett et al. |

OTHER PUBLICATIONS

Hoshi et al.; "A total synthesis of 6, 7-dihydroeponemycin and determination of stereochemistry of the epoxide ring"; *Tetrahedron Letters*; (1993); 34(6): 1047-50.
Crews et al.; "Natural products as molecular probes of angiogenesis"; *Book of Abstracts*, 215th ACS National Meeting, Dallas, Mar. 29-Apr. 2, 1998, MEDI-208 Publisher: American Chemical Society, Washington, D.C.
Sin et al.; "Eponemycin analogs: syntheses and use as probes of angiogenesis"; *Bioorganic & Medicinal Chemistry*; (1998); 6(8): 1209-1217.
Meng et al.; "Eponemycin exerts its antitumor effect through the inhibition of proteasome function"; *Cancer Research*; (1999); 59(12): 2798-2801.
Kim et al.; "Proteasome inhibition by the natural products epoxomicin and dihydroeponemycin: insights into specificity and potency"; *Bioorganic & Medicinal Chemistry Letters*; (1999); 9(23): 3335-3340.
Bennacer et al.; "A new route for the total synthesis of 6, 7-dihydroeponemycin"; *European Journal of Organic Chemistry*; (2003); (23): 4569-4574.
Akasaka et al.; "Novel epoxyketone proteasome inhibitors: Synthesis and SAR study"; *Abstracts of Papers*, 227th ACS National Meeting, Anaheim, CA, Mar. 28-Apr. 1, 2004.
Ho et al.; "Towards immunoproteasome-specific inhibitors: An improved synthesis of dihydroeponemycin"; *European Journal of Organic Chemistry*; (2005); (22): 4829-4834.
Kim et al.; "Development and characterization of proteasome inhibitors"; *Methods Enzymol.*; (2005); (399): 585-609.

*Primary Examiner*—Shailendra Kumar
(74) *Attorney, Agent, or Firm*—Stites & Harbison PLLC; Stephen J. Weyer; Mandy W. Decker

(57) ABSTRACT

An efficient new route for the preparation of dihydroeponemycin, an active eponemycin derivative, is provided, which includes the synthesis of the intermediate compound, a hydroxymethyl-substituted enone. In addition, a method is provided for synthesizing inhibitors, which includes PI'-modified analogues. These analogues selectively bind to a major immunoproteasome catalytic subunit LMP2 and inactivate its proteolytic activity in a method of treating diseases, including myeloma and other cancers, Huntington's disease and Alzheimer's disease.

14 Claims, 2 Drawing Sheets

EPOXYKETONE-BASED IMMUNOPROTEASOME INHIBITORS

FIELD OF THE INVENTION

The present method relates to epoxyketone-based immunoproteasome inhibitors and, in particular, to the synthesis of the inhibitors, their intermediaries, and treatment of disease using the inhibitors.

BACKGROUND OF THE INVENTION

Intracellular protein degradation is a highly regulated process in which proteins are first targeted for degradation by conjugation to ubiquitin, a 76 amino acid polypeptide. Ubiquitinated proteins are then recognized by the 19S regulatory domain of the 26S proteasome. Through a series of ATP hydrolysis-dependent processes, targeted proteins are deubiquitinated and threaded into the core proteolytic complex, the 20S proteasome, where they are degraded into small peptides. Interestingly, exposure of cells to stimuli, such as interferon (IFN)-γ, tumor necrosis factor (TNF)-α and lipopolysaccharide (LPS), induces the synthesis of certain catalytic subunits (LMP2, MECL-1 and LMP7) that together are incorporated into alternative proteasome form, known as the immunoproteasome.

The immunoproteasome, as compared to the constitutive proteasome, has an enhanced capacity to generate peptides bearing hydrophobic and basic amino acids at their C-termini, and a reduced capacity to produce peptides bearing acidic residues at their C-terminus. Consequently, the spectrum of the produced peptides is shifted towards peptides which associate with MHC class I molecules with increased affinity, implicating a major role in antigen presentation. Immunoproteasome may be involved in some pathological processes, such as diabetes and autoimmune diseases. Therefore, development of immunoproteasome-specific inhibitors would be useful to investigate the role of immunoproteasome and to determine whether immunoproteasome is a potential target for development of pharmaceutical agents.

Scheme 1. α',β'-Epoxyketone linear peptide natural products, epoxomicin and eponemycin, and eponemycin analogues.

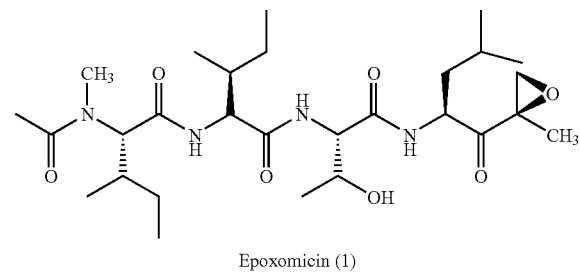

Epoxomicin (1)

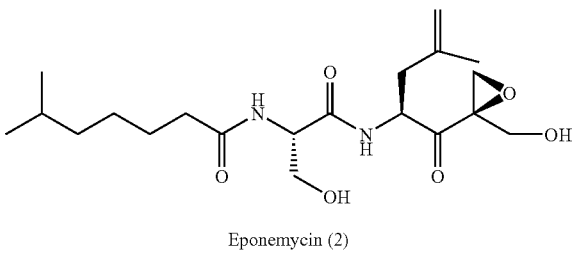

Eponemycin (2)

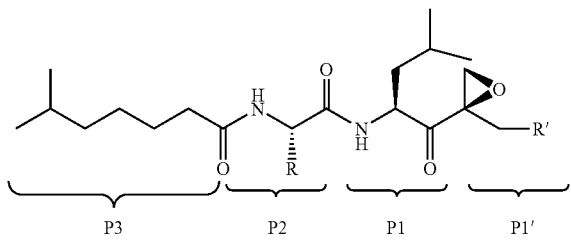

Dihydroeponemycin (3)
R = ——CH$_2$OH, R' = OH
(4) R = alkyl, R' = C—— or O—— alkyl groups
(5) R = CH$_3$; R' = OH Anti-tumor natural products epoxomicin (1) and eponemycin (2) are members of linear peptides containing α',β'-epoxyketone pharmacophore and have been shown to exert their anticancer activity through proteasome inhibition. Of particular interest was the finding that, despite structural similarities, epoxomicin (1) and dihydroeponemycin (3), an active derivative of eponemycin, differ in their proteasome subunit binding specificity.

Moreover, unlike other classes of proteasome inhibitors that show non-target specificity, the epoxyketone proteasome inhibitor is shown to be highly specific for the 20S proteasome. The crystal structure of the yeast 20S proteasome complexed with epoxomicin revealed that the unique specificity of epoxyketone pharmacophore is contributed to the formation of an unusual 6-membered morpholino ring between the amino terminal catalytic Thr-1 of the 20S proteasome and the (α',β'-epoxyketone pharmacophore of epoxomicin, as shown in the mechanism below.

Proposed mechanism of proteasome inhibition by an epoxyketone natural product epoxomicin.

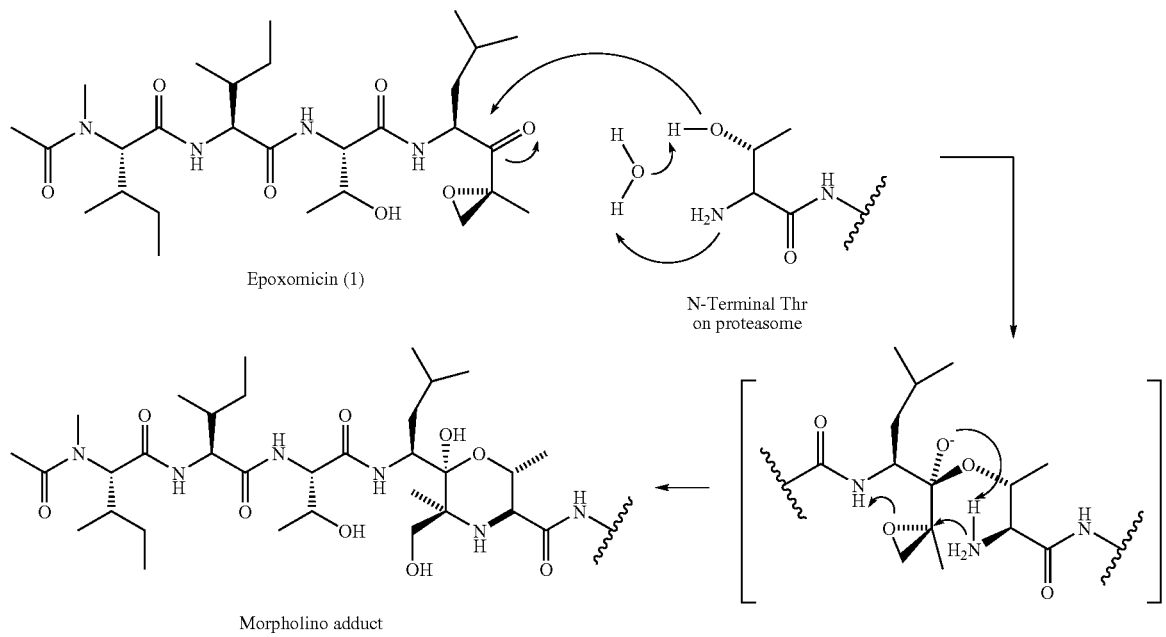

In addition, it has been shown that dihydroeponemycin (3) targets the subunits of both constitutive proteasome and immunoproteasome, whereas epoxomicin (1) preferentially labels the catalytic subunits of the constitutive proteasome. Recent studies indicated that the ability of dihydroeponemycin to bind immunoproteasome subunits is attributed to the P3 isooctanoic moiety of dihydroeponemycin but not the hydroxyl groups in the P2 and P1' positions (see scheme 1). Therefore, isooctanoic-based dihydroeponemycin analogue (4) or other dihydroeponemycin analogues having a linear hydrocarbon group at the P3 position may provide an opportunity for the development of immunoproteasome-specific inhibitors. However, a simple and practical approach for the synthesis of dihydroeponemycin has yet to be developed. Particularly, the lack of the efficient synthetic approach for the hydroxymethyl-substituted enone motif has been a major obstacle for efficient synthesis of dihydroeponemycin and their P1' derivatives (4).

Over the years, a number of elegant synthetic strategies for the synthesis of eponemycin and dihydroeponemycin have been developed. A key step in the synthesis is the preparation of hydroxymethyl-substituted enone 10 (Scheme 2). In several earlier approaches, the enone 10 was prepared from the reaction of dilithio reagent 8 with the corresponding aldehyde (Scheme 2). However, low yields and extra steps involving protection, oxidation and deprotection of OH groups prevented large scale preparation. In similar approaches, the Weinreb-type amide derivatives treated with dilithio reagent 8 did not yield the desired hydroxymethyl-substituted enone 10. More recently, new synthetic approaches have been developed based on the cinchona alkaloid-catalyzed Baylis-Hillman type reactions that yield the intermediate 7 or Stille coupling of Fmoc-Leu-Cl with n-tributylvinyltin followed by modified Baylis-Hillman reaction (Scheme 2).

Scheme 2. Synthetic strategies for the preparation of α-hydroxymethyl-substituted enone.

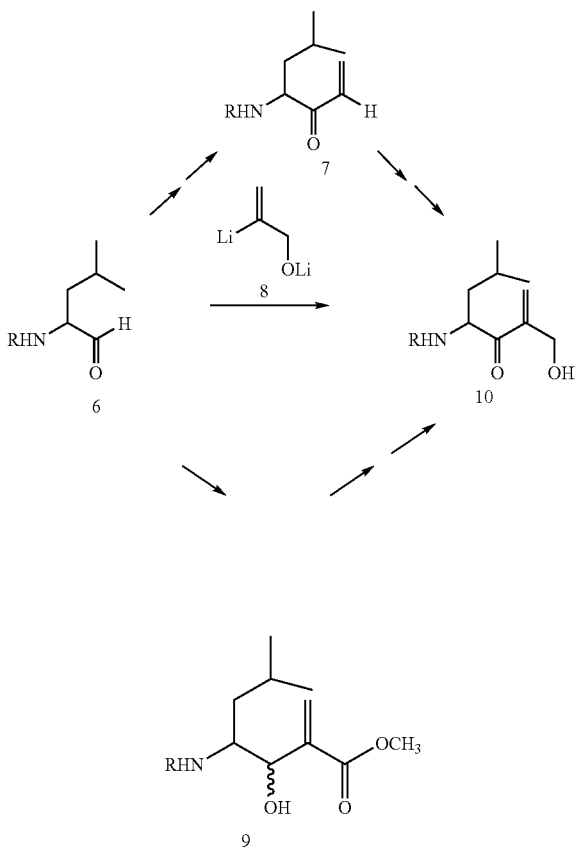

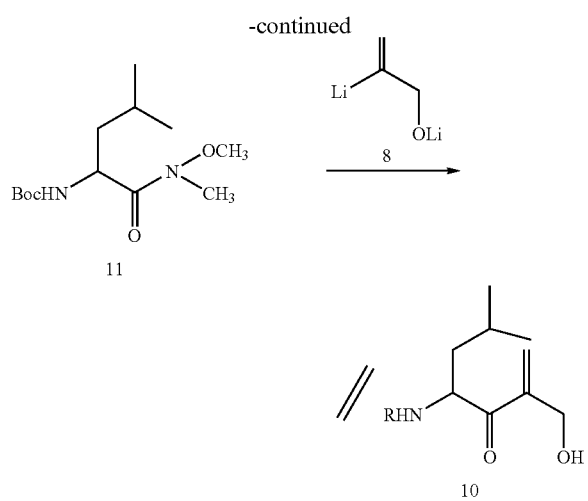

However, multiple steps and low yields associated with these approaches may not be ideal for efficient derivatization or construction of small library of dihydroeponemycin analogues for screening immunoproteasome-specific inhibitors.

Over the past decades, the proteasome has emerged as a major player in many important signaling processes such as cell cycle progression, inflammatory responses and development. In particular, the fact that the orderly destruction of cell cycle regulatory proteins is critical to the control of cellular processes associated with cancer has led to development of proteasome inhibitors as anti-cancer agents, leading to a recent FDA approval of the first proteasome inhibitor bortezomib for multiple myeloma. Typically, more than 80% of cellular proteins are targeted for recognition and subsequent degradation by the proteasome via the attachment of multiple ubiquitin molecules.

The 20S core has a four-stacked ring structure with seven different subunits in each ring. The two inner rings each contain three catalytically active β subunits. The non-catalytic two outer α rings form a gated channel for unfolded protein entry and a base for the regulatory complexes (19S or 11S), which provide the specificity of the polypeptide recognition.

The 20S proteasome has been shown to exhibit three major activities: a chymotrypsin-like (CT-L) activity that cleaves after large hydrophobic residues, a trypsin-like (T-L) activity that hydrolyzes after basic amino acids, and a caspase-like (C-L) activity that cleaves after acidic amino acids. Two other less-characterized catalytic activities have also been ascribed to the proteasome: BrAAP, which cleaves after branched-chain amino acids, and SNAAP, which cleaves after small neutral amino acids. Thus far, while most efforts are directed to develop proteasome inhibitors against chymotrypsin-like activity, a few studies have been successful to design inhibitors targeting other proteasomal activities, such as caspase-like and trypsin-like activities. Although the CT-L activity of the proteasome has been shown to be largely responsible for the proteolytic function of the proteasome in vivo and in vitro, the contribution of other major activities remains to be determined.

While the immunoproteasome is widely known to play a major role in MHC class-I antigen presentation, it is believed not to be solely responsible for antigen presentation as the constitutive proteasome also generates immunogenic epitopes.

Recently, intense investigation on the role of immunoproteasome in cells from non-immune system has been initiated based on a number of studies indicating that immunoproteasome subunits may be implicated in some pathological processes, such as hematological cancers, autoimmune diseases and neurodegenerative diseases. For example, a high level of immunoproteasome has been detected in neurodegenerative human brains, whereas the human brain has been historically considered as an immunologically privileged organ. Specifically, it has been shown that the immunoproteasome is more highly expressed in the brains of Alzheimer's disease (AD) than in brains of non-demented elderly, whereas its expression in young brains is negligible or absent. In addition, some studies indicated that the immunoproteasome may be involved in Huntington's disease (HD) neurodegeneration. Multiple myeloma is also known to express a high level of immunoproteasome due to its bone marrow microenvironment where it replicates. Recently bortezomib (VELCADE®), the first proteasome inhibitor was approved by the FDA for the treatment of multiple myeloma. Despite this remarkable advancement, its clinical use is severely limited due to drug-related toxicities. Given this, specific inhibition of immunoproteasome should allow selective killings of multiple myeloma cells while sparing other cells in body that are lacking or minimally expressing the immunoproteasome.

Despite the potential role of immunoproteasome in these pathological disorders, its functions are still not clearly understood. Currently, there are no immunoproteasome specific inhibitors which are therapeutic agents, targeting the immunoproteasome. Furthermore, the exact role of immunoproteasome in pathogenesis is not clearly understood, due largely to the lack of an appropriate molecular probe.

Although some proteasome inhibitors currently exist that selectively target the immunoproteasome, and a sequence comparison of catalytic subunits from the constitutive and immunoproteasomes exhibits a high homology, structural information about active sites of immunoproteasome are not known to date, hindering prior efforts towards the design of immunoproteasome-specific inhibitors via rational design approach, to be therapeutic agents.

Scheme 3. Structures of α', β', -epoxyketone linear peptide natural products and dihydroeponemycin analogues. Tripeptide epoxyketones having a linear hydrocarbon chain at the P3 position has a higher specificity towards immunoproteasome catalytic subunits than normal tetrapeptide epoxyketones such as epoxomicin.

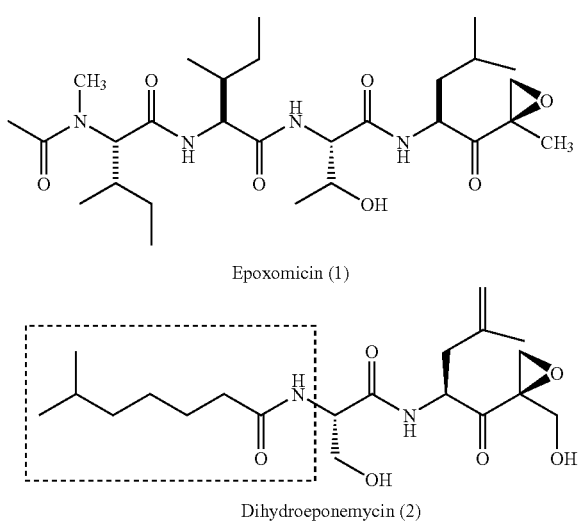

-continued

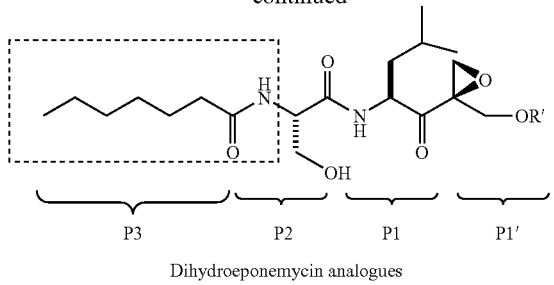

Dihydroeponemycin analogues

Two natural product proteasome inhibitors, epoxomicin and eponemycin, are members of the α',β'-epoxyketone linear peptide family. It has been previously shown that, despite structural similarities, epoxomicin (1) and dihydroeponemycin (2), an active derivative of eponemycin, considerably differ in their proteasome subunit binding specificity. For example, dihydroeponemycin preferentially labels the catalytic threonine residues of immunoproteasome subunit LMP2 and to a lesser degree, the constitutive proteasome subunit X and immunoproteasome subunit LMP7. On the other hand, epoxomicin covalently modifies the N-terminus catalytic threonine residues of both the constitutive proteasome (X & Z) and immunoproteasome (LMP7 & MECL1) to a similar extent. It has been shown that a relatively higher specificity of dihydroeponemycin towards the immunoproteasome subunits as compared to epoxomicin is due to a linear hydrocarbon residue at the N-terminus (i.e., isooctanoic group). Recently, it has been shown that serine at the P2 site can be replaced with alanine while maintaining the same subunit binding pattern as dihydroeponemycin. More interestingly, careful analysis of other reports indicates that a residue at the P1' site may be an important determinant for immunoproteasome subunit binding.

SUMMARY OF THE INVENTION

The present invention is directed to a new and improved route to the synthesis of a hydroxymethyl-substituted enone and dihydroeponemycin (3).

The present invention is also directed to the synthesis of proteasome inhibitors that selectively target the immunoproteasome. These proteasome inhibitors comprises a variety of P1'-modified dihydroeponemycin analogues using easily available protecting groups. The present dihydroeponemycin analogues selectively bind to a major immunoproteasome catalytic subunit LMP2 and inactivate the proteolytic activity of immunoproteasome with high specificity. The proteasome inhibitors are therapeutic agents which selectively target the immunoproteasome, and thereby treat diseases, including cancer, Alzheimer's disease and Huntington's disease.

The present invention, in one form thereof, relates to a method for synthesizing a hydroxymethyl-substituted enone, comprising (a) reacting Boc-Leu-OMe with dimethyl methylphosphonate treated with tert-butyllithium to form the compound,

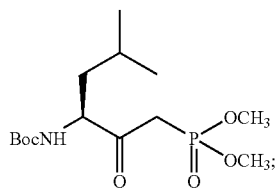

and (b) adding $CH_2O$ and $K_2O_3$ to the product of step (a) and allowing the reagents to react to produce the hydroxymethyl-substituted enone,

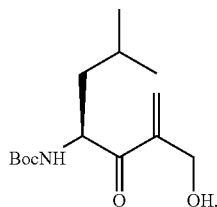

The present method, in a further, specific form thereof, further comprises (c) adding TBDMSCl, Imidazole and $CH_2Cl_2$ to the hydroxymethyl-substituted enone from step (b); (d) adding benzonitrile, $H_2O_2$, i-$Pr_2EtN$ and $CH_3OH$; (e) adding TFA and $CH_2Cl_2$; and (f) adding

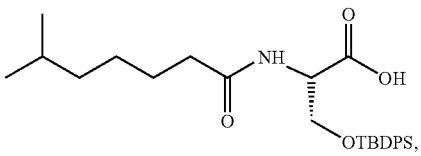

HBTU, HoBt, i-$PR_2EtN$ and $CH_2Cl_2$, followed by TBAF and THF to produce dihydroeponemycin,

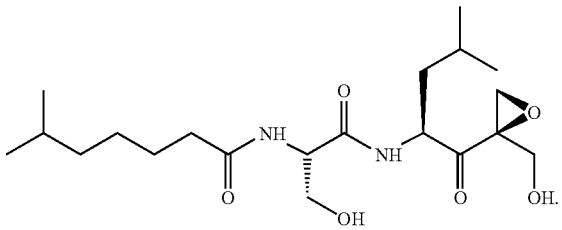

The present invention, in another form thereof, relates to a P1' modified dihydroeponemycin analogue comprising

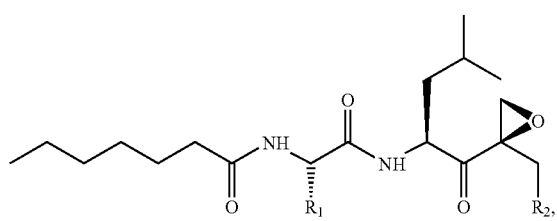

where:
$R_1$ is $CH_3$ or $CH_3OH$; and $R_2$ is OH,

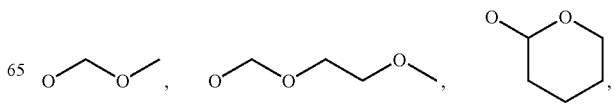

-continued

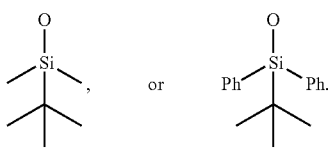

The present invention, in another form, thereof, relates to a method for manufacturing a P1' modified dihydroeponemycin analogue, comprising (a) reacting a hydroxymethyl-substituted enone,

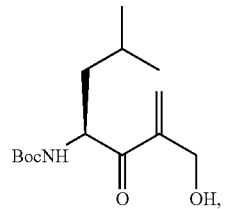

with 2-methoxyethoxymethyl chloride, i-Pr$_2$EtN, CH$_2$Cl$_2$; (b) adding benzonitrile, H$_2$O$_2$, i-Pr$_2$EtN, CH$_3$OH; (c) adding TFA, CH$_2$Cl$_2$; and (d) adding HBTU, HoBt, i-Pr$_2$EtN, CH$_2$Cl$_2$, and

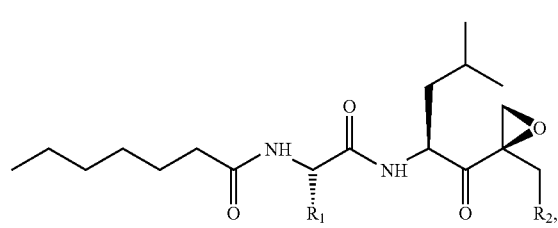

to produce P1' modified dihydroeponemycin analogue of formula I (I)

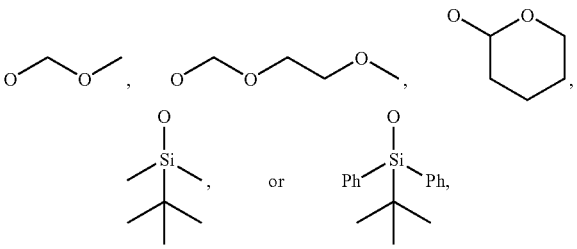

where:
R$_1$ is CH$_3$ or CH$_3$OH; and
R$_2$ is OH,

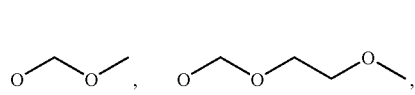

-continued

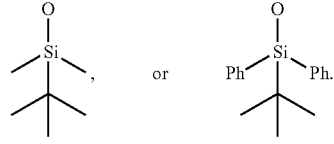

In one specific compound, R$_1$ is CH$_3$ and R$_2$ is

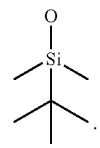

The present invention, in yet another form thereof, relates to a method of inactivating enzymatic activity of catalytic subunit LMP2 of the immunoproteasome, comprising reacting a P1' modified dihydroeponemycin analogue, (I)

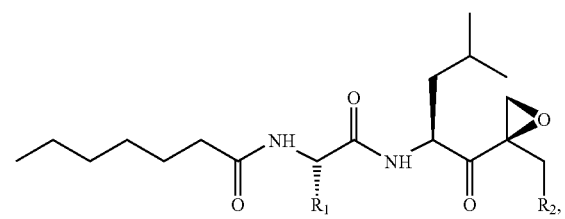

where R$_1$ is CH$_3$ or CH$_3$OH; and R$_2$ is OH, with the catalytic subunit LMP2.

The present invention, in anther form thereof, relates to a method for treating disease by administering to a patient an effective amount of a dihydroeponemycin analogue having the formula I (I)

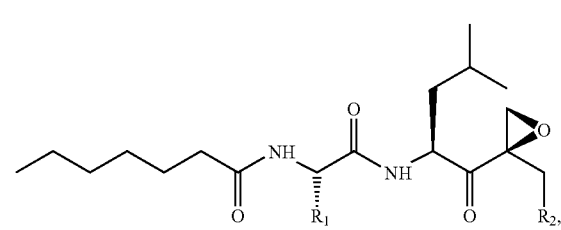

where:
R$_1$ is CH$_3$ or CH$_3$OH; and
R$_2$ is OH,

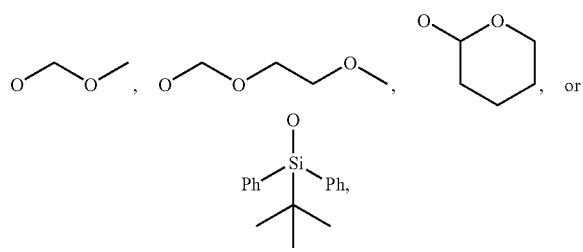

to bind to the LMP2 subunit of the immunoproteasome, thereby treating the disease. In various, specific further embodiments, the disease is selected from the group consisting of myeloma, Alzheimer's disease, and Huntington's disease; and $R_1$ is $CH_3$ and $R_2$ is

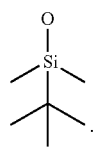

The present invention, in yet another form thereof, relates to a method of inactivating the immunoproteasome, comprising administering to a patient in need of treatment thereof, an effective amount of a dihydroeponemycin analogue of formula I,

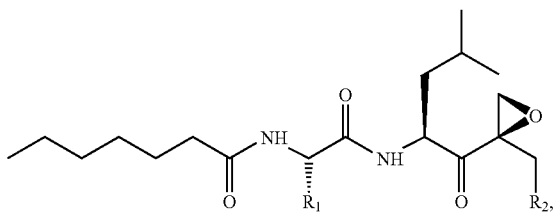

where $R_1$ is $CH_3$ or $CH_3OH$; and $R_2$ is OH,

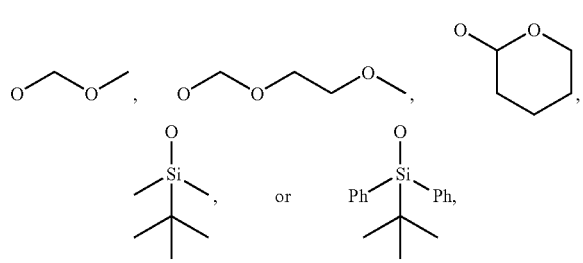

to bind to LMP2 of the immunoproteasome, to thereby inactivate the immunoproteasome.

DETAILED DESCRIPTION

Figure 1:
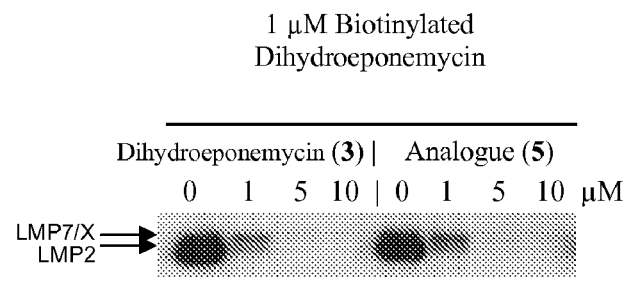
FIG. 1 is a western blot showing dihydroeponemycin binding to both constitutive- and immunoproteasome catalytic subunits, in accordance with the present invention.

The present invention is directed to a new and improved route to the synthesis of the hydroxymethyl-substituted enone and dihydroeponemycin (3). The hydroxyl group, commonly present in both eponemycin and epoxomicin at the P2 position, is not required for immunoproteasome binding.

In addition, the present invention is directed to a method of synthesizing dihydroeponemycin analogues having the general formula I

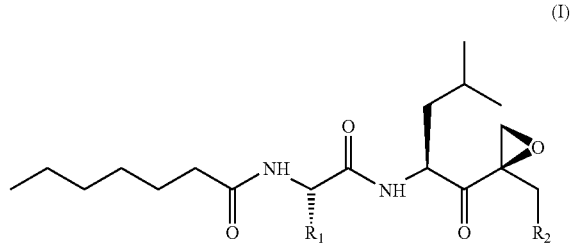

where
$R_1$ is $CH_3$ or $CH_3OH$, and
$R_2$ is OH,

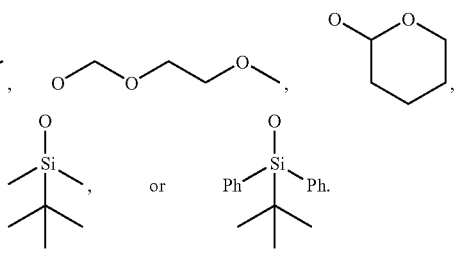

The present invention is also directed to a method of treatment comprising administering to a patient in need to treatment thereof, a therapeutically effective amount of a dihydroeponemycin analogue, having the general formula I, to bind to the LMP2 subunit of the immunoproteasome, thereby treating the disease. The treated diseases include myeloma, Alzheimer's disease, and Huntington's disease.

The preferred dose for administration of the immunoproteasome inhibitor, in accordance with the present invention, is that amount which will be effective in preventing or treating cancer, such as myeloma, Alzheimer's disease, or Huntington's disease, by lowering or inhibiting LMP2 catalytic activity, by binding to the LMP2 subunit, and one would readily recognize that this amount will vary greatly depending on the nature and extent of the disease and the condition of a patient. An "effective amount" of the inhibitor to be used in accordance with the invention is intended to mean a nontoxic but sufficient amount of the agent, such that the desired prophylactic or therapeutic effect is produced. Thus, the exact amount of the inhibitor that is required will vary from subject to subject, depending on the species, age, and general condition of the subject, the severity of the condition being treated, the particular carrier or adjuvant being used and its mode of administration, and the like. Similarly, the dosing regimen should also be adjusted to suit the individual to whom the composition is administered and will once again vary with age, weight, metabolism, etc. of the individual. Accordingly, the "effective amount" of any particular inhibitor will vary based on the particular circumstances, and an appropriate effective amount may be determined in each case of application by one of ordinary skill in the art using only routine experimentation.

The present method provides an efficient, practical synthetic strategy for the synthesis of hydroxymethyl-substituted enone and dihydroeponemycin. The present method starts with readily available Boc-Leu-OMe, which was prepared from the reaction of Boc-Leu-OH with iodomethane in DMF. The reaction of Boc-Leu-OMe with dimethyl methylphosphonate treated with t-butyllithium yielded compound 13. Finally, the combination of Wittig-Horner and Baylis-Hillman type one-pot reactions yielded the hydroxymethyl-substituted enone 14 in high yield (Scheme 4).

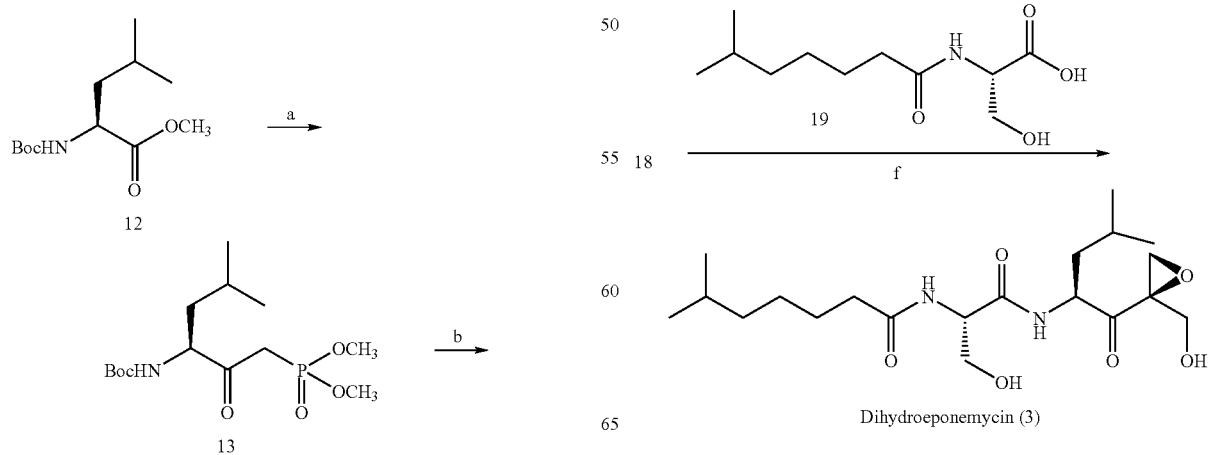

Scheme 4. Reagents and conditions: (a) i. CH$_3$PO(OCH$_3$)$_2$, BuLi, THF, -78° C., 2 h; ii. 12, THF, -78° C., 3 h; (b) CH$_2$O, K$_2$CO$_3$, H$_2$O, rt, 3 h; (c) TBDPSCl, Imidazole, CH$_2$Cl$_2$, rt, 24 h; (d) Benzonitrile, H$_2$O$_2$, i-Pr$_2$EtN, MeOH, 0° C., 3 h; (e) TFA, CH$_2$Cl$_2$, rt, 15 min; (f) i. 19. HBTU, HoBt, i-Pr$_2$EtN, CH$_2$Cl$_2$, rt, 12 h; ii. TBAF, THF, rt, 10 min.

The resulting hydroxymethyl substituted enone was treated with TBDPSCl to yield compound 15. Epoxidation of compound 15 with hydrogen peroxide afforded two epoxyketone isomers 16 and 17 as a 1:1.5 mixture which were readily separated by flash column chromatography using an elution system (hexanes-ethyl acetate=10:1, v/v). The isomer (2-(R)-epoxide) 17, which migrates faster than the 2-(S)-epoxide 16 in thin-layer chromatography (TLC), was found to have the same configuration as that of eponemycin epoxide. The final coupling reaction between epoxyketone 18 and dipeptide 19 was performed with HBTU, followed by removal of the TBDPS group and normal phase HPLC (hexanes-isopropanol, linear gradient, hexanes 100% to 50%) to yield dihydroeponemycin (3).

As compared to prior art methods of synthetic strategies, the combination of Wittig-Horner and Baylis-Hillman type two-step "one-pot" reaction presented here is efficient and practical for a large quantity preparation, easily providing the key intermediate, hydroxymethyl-substituted enone, in a multi-gram scale. The one-pot reaction may be rationalized by the following mechanistic consideration (Scheme 5).

The synthesis steps for dihydroeponemycin derivatives can be further reduced as the serine residue of dihydroeponemycin needs to be protected and the alanine residue of its analogue does not as show in "Towards Immunoproteasome-Specific Inhibitors: An Important Synthesis of Dihydroeponemycin" Abby Ho et al., *Eur. J. Org. Chem.* (2005), herein incorporated by reference.

The present invention is also directed to the synthesis of proteasome inhibitors that selectively target the immunoproteasome. These proteasome inhibitors comprises a variety of P1'-modified dihydroeponemycin analogues using easily available protecting groups (Scheme 6).

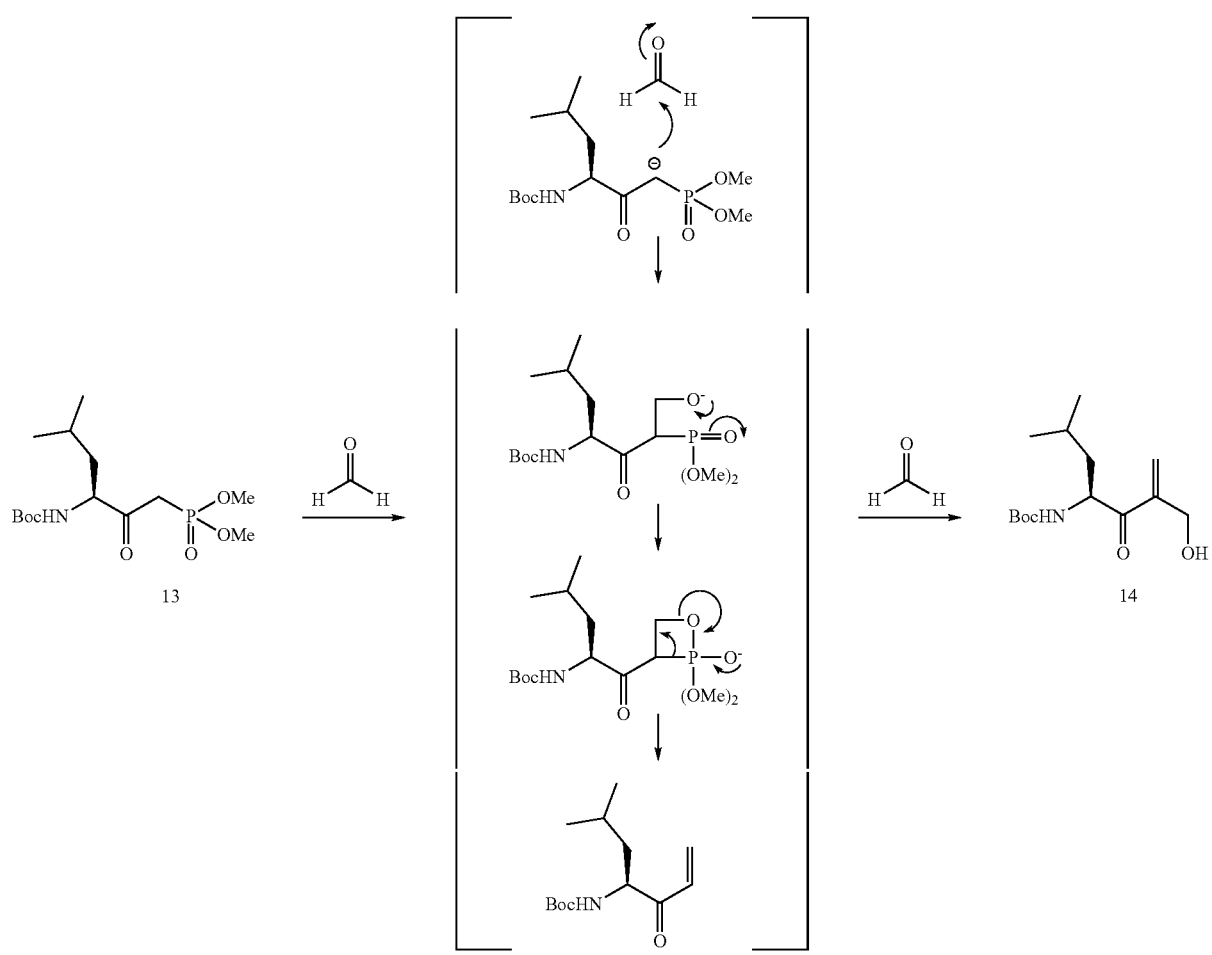

Scheme 5.
Mechanistic consideration for the one-pot reaction that may occur sequentially through the Wittig-Horner and Baylis-Hillman type reactions.

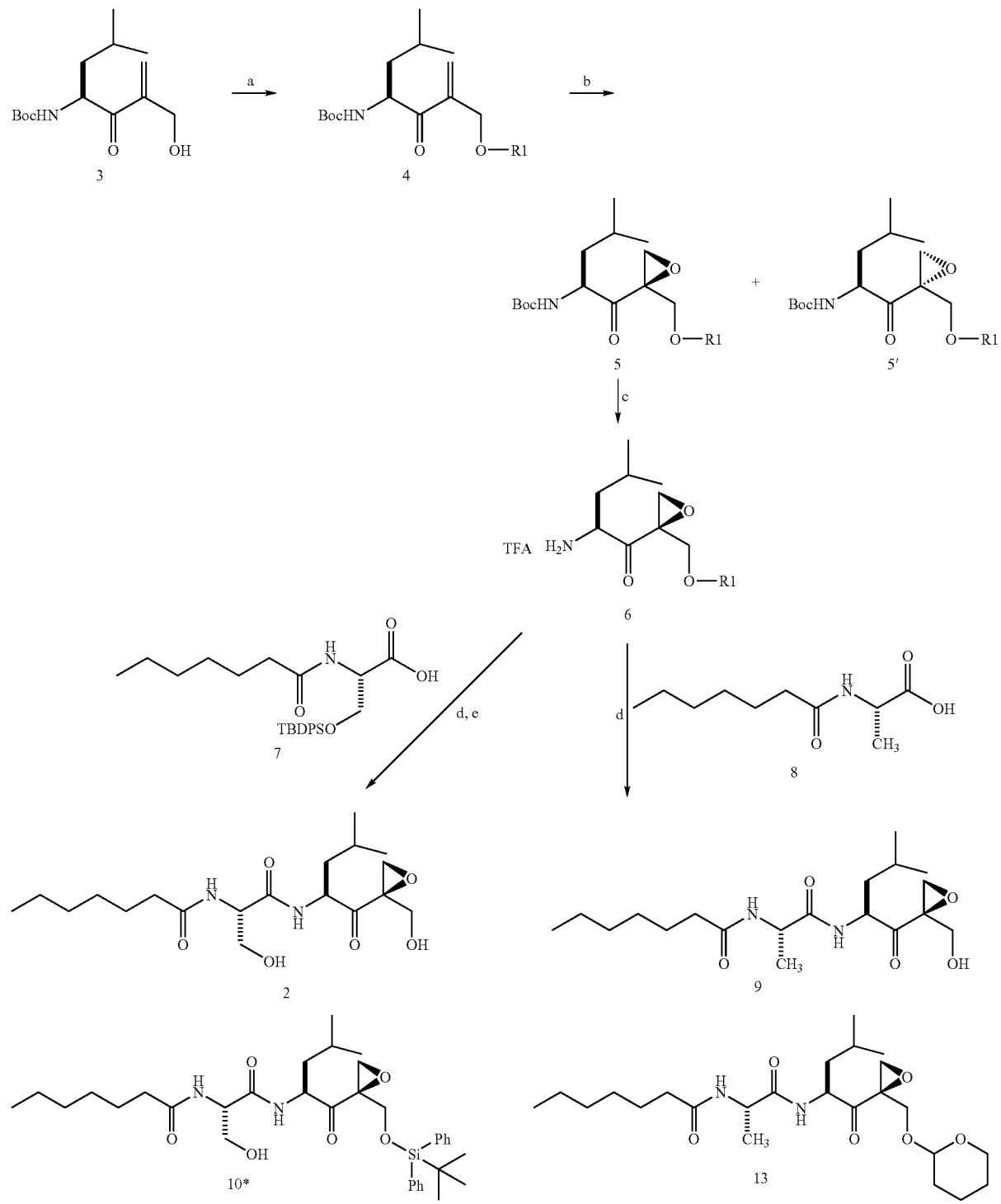
Scheme 6.
Synthetic scheme of dihydroeponemycin analogues. Reagents and conditions for 12.
(a) 2-Methoxyethoxymethyl Chloride, i-Pr₂EtN, CH₂Cl₂, 0° C. → rt;
(b) Benzonitrile, H₂O₂, i-Pr₂EtN, CH₃OH, 0° C., 3 h; (c) 5, TFA, CH₂Cl₂, 30 min;
(d) 7, HBTU, HoBt, i-Pr₂EtN, CH₂Cl₂, rt, 12 h; (e) TBAF, THF, 1 h.
*(e) precedes (d): 7 was deprotected with TBAF before coupled to 6.

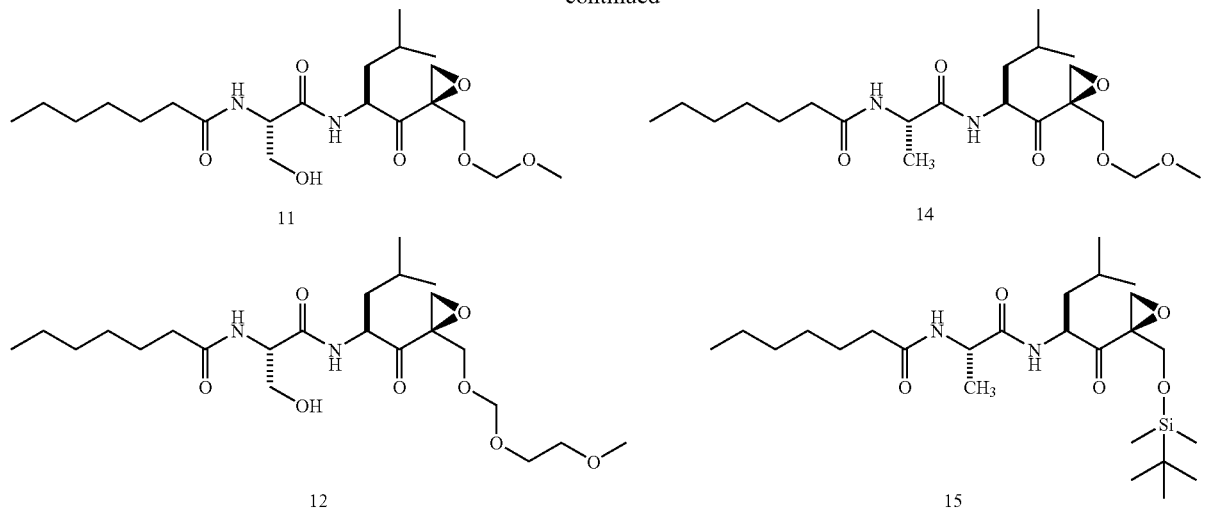

The present dihydroeponemycin analogues selectively bind to a major immunoproteasome catalytic subunit LMP2 and inactivate the proteolytic activity of immunoproteasome with high specificity.

To test the specificity of binding of the present dihydroeponemycin analogues, a screening assay was developed for immunoproteasome subunit specific compounds Biotin-tagged epoxomicin and dihydroeponemycin were used as assay probes with which to perform screening assay for immunoproteasome subunit-specific compounds. The screening assay was first verified by using epoxmicin, dihydroeponemycin and eponemycin analogue whose proteasome subunit binding patterns are well known from Kim, K. B., Myung, J., Sin, N., and Crews, C. M. "Proteasome inhibition by the natural products epoxomicin and dihydroeponemycin: insights into specificity and potency," Bioorg. Med. Chem. Lett. 9, 3335-3340 (1999) (herein incorporated by reference); and "Towards Immunoproteasome-Specific Inhibitors: An Improved Synthesis of Dihydroeponemycin." Specifically, various concentrations of these compounds were pre-incubated in EL4 cells at 37° C. for 30 min. Biotin-tagged dihydroeponemycin or epoxomicin were then added and incubated for an additional hour at 37° C. After cells were lysed, whole cell lysates were analyzed using 12% SDS-PAGE and transferred to PVDF membranes. Biotinylated proteins were then visualized using streptavidin-horseradish peroxidase (HRP) and enhanced chemiluminescence (ECL).

Figure 2:
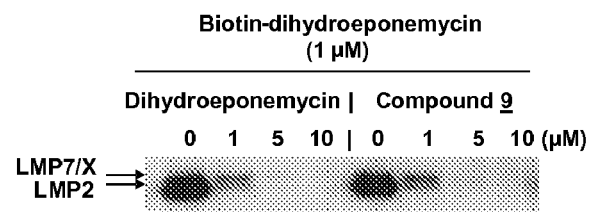
FIG. 2(a) is a western blot showing LMP7/X and LMP2 protein bands are competed away by dihydroeponemycin (2) and its analogue (9)
FIG. 2(b) is a western blot showing proteasome subunit (Z, MECL1, LMP7 and X) bands are efficiently competed away by excess epoxomicin on western blot, in accordance with the present invention.
Figure 2:
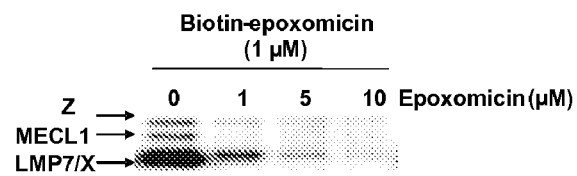

Referring to FIG. 2(a), a western blot which shows LMP7/X and LMP2 protein bands are competed away by dihydroeponemycin (2) and its analogue compound 9. FIG. 2(b) is a western blot which shows proteasome subunit (Z, MECL1, LMP7 and X) bands are efficiently competed away by excess epoxomicin. The western blots were performed using EL4 cells pre-incubated with proteasome inhibitors for 30 min before treating with biotinylated compounds. After 1 hr incubation, cells were lysed, and analyzed by western blot using streptavidin-HRP and ECL.

All of biotinylated proteasome subunit bands were equally competed away with excess dihydroeponemycin, its analogue or epoxomicin. These results confirm that both epoximicin and dihydroeponemycin do not have specificity towards subunits of either the constitutive or immunoproteasomes. In addition to these two compounds, an analogue of dihydroeponemycin, in which the P2 serine of eponemycin is replaced with alanine, displayed a non-specific proteasome subunit binding pattern similar to that of dihydroeponemycin.

Similar competition assays were performed to screen for immunoproteasome inhibitors in a EL4 cell model system. EL4 cell system was chosen since these cells highly express catalytic subunits of both the constitutive and immunoproteasomes.

Figure 3:
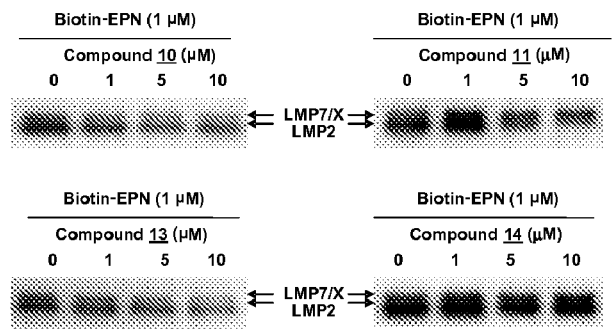
FIG. 3 is a western blot showing compounds 10, 11 and 13 do not selectively target proteasome subunits, and compound 14 does not covalently modify proteasome subunits, in accordance with the present invention.

Given the previous studies suggesting that the N-terminus hydrocarbon group plays an important role in targeting the immunoproteasome (29), the present inhibitors were developed based on the derivatization at the C-terminal hydroxyl group (Scheme 6). First, methoxymethyl ether (MOM) group was added, preparing compounds 11 and 14. This replacement caused a dramatic loss in the potency and specificity compared to dihydroeponemycin (FIG. 3). Similarly, dihydroeponemycin analogues with a bulky tert-butyldiphenylsilyl (TBDPS) group (10) or tetrahydropyranyl (THP) group (13) lost its activity against the immunoproteasome (FIG. 3).

Figure 4:
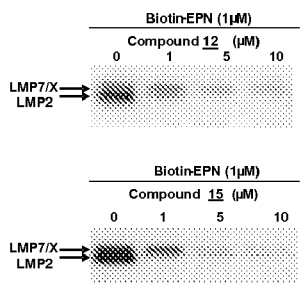
FIG. 4(a) is a western blot depicting compounds 12 and 15 selectively targeting the immunoproteasome subunit LMP2 in EL4 cells.
FIG. 4(b) is a western blot showing compounds 12 and 15 do not covalently modify the proteasome subunits that are normally labeled by epoxomicin, indicating that these compounds do not target subunits such as Z, MECL-1, LMP7 and X, in accordance with the present invention.
Figure 4:
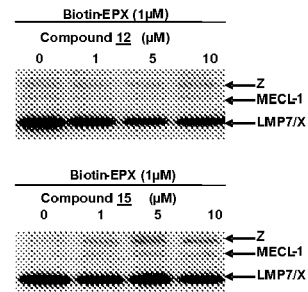

Strikingly, when the MOM group was replaced with methoxyethoxymethyl (MEM) ether group (12), which has a longer linear group than the MOM group, high specificity towards LMP2 was achieved (upper panel of FIG. 4(a)). Intriguingly, when the bulky TBDPS group was replaced with a less bulky tert-butyldimethylsilyl (TBDMS) group (15), an even higher specificity towards the LMP2 subunit was obtained, as shown in FIG. 4(a) (lower panel). Preincubation of EL4 cells with 1 μM of compound 15 (one equivalent of assay probe) was sufficient to selectively modify the catalytic threonine residue of LMP2 subunit, thereby preventing further modification of LMP2 subunit by biotin-dihydroeponemycin, resulting in selective attenuation of LMP2 protein band on western blot. Experiments with another assay probe (biotin-epoxomicin), which normally labels proteasome subunits LMP7, X, MECL-1 and Z, further supported that both compounds 12 and 15 specifically target LMP2 subunit but not other proteasome subunits (FIG. 4(b)). These results further confirm that compounds 12 and 15 are specific LMP2 inhibitors.

Figure 5:
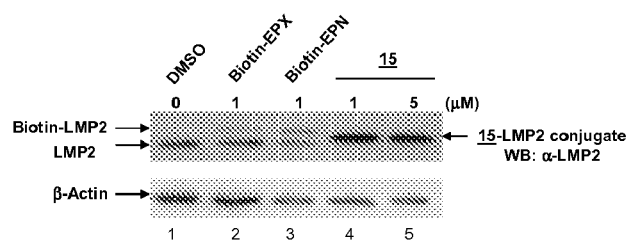
FIG. 5 is a western blot depicting compounds 15 covalently modify the immunoproteasome subunit LMP2.

The mobility shift of LMP2:15 adduct was investigated to further verify that compound 15 covalently modifies the LMP2 subunit (FIG. 5). After EL4 cells were incubated with compound 15 or assay probes (Biotin-EPX and Biotin-EPN)

for 1 hr at 37° C., cells were lysed and boiled for 15 min. Whole cell proteins were then analyzed by western blot using anti-LMP2 antibody. In this experiment, biotinylated epoxomicin (Biotin-EPX) and dihydroeponemycin (Biotin-EPN) were used as controls that induce LMP2 mobility shift.

Since molecular weights of the LMP2 subunit are increased by 828.08 (for biotin-epoxomicin) and 1078.45 (for biotin-dihydroeponemycin), assay probe-LMP2 adducts are expected to show a slower mobility as compared to free LMP2 (lanes 1-3, FIG. 5). While a slower mobility for the LMP2-15 adduct on SDS PAGE was clearly shown as compared to free LMP2 (lanes 4 and 5), its mobility shift was smaller than those of assay probe-LMP2 adducts (lane 3 vs. lane 4). It can be explained by a smaller molecular weight of compound 15 (484.76) compared to assay probes (828.08 and 1078.45). Interestingly, 1 µM of compound 15 but not assay probes was sufficient to modify LMP2 subunits present in cells (lanes 2 & 3 vs 4). This strongly indicates that compound 15 modifies the LMP2 subunit more efficiently than two assay probes. LMP2 inhibitor efficiently blocks the proteolytic activity of immunoproteasome with high specificity. Screening assay and mobility shift studies have shown that compound 15 selectively inactivates the LMP2 subunit via covalent modification. Since LMP2 is a major catalytic subunit responsible for chymotrypsin-like activity, inactivation of the LMP2 subunit inhibits proteolytic activity of immunoproteasome. Confirmation of this is provided by enzyme kinetics studies performed using purified 20S immunoproteasome. Enzyme kinetics experiments were also carried out with the purified 20S constitutive proteasome as control.

TABLE 1

Inhibition of chymotrypsin-like activity of the 20S constitutive and immunoproteasomes by compound 15.

| Compounds | $K_{obs}/[I]$ $(M^{-1}S^{-1})^a$ | | Relative selectivity[c] |
|---|---|---|---|
| | 20S regular proteasome | 20S immunoproteasome | |
| Epoxomicin | 44,510 ± 7,000 (25-75 nM)[b] | 3,044 ± 1,423 (100-400 nM) | 1 |
| Dihydroeponemycin | 721 ± 84 (0.25-5 µM) | 251 ± 121 (0.5-3.0 µM) | 5 |
| Compound 15 | 49 ± 18 (10-50 µM) | 83 ± 27 (5-20 µM) | 24 |

[a]See Experimental Procedures for details.
[b]Values in parentheses indicate the range of inhibitor concentrations used.
[c]Relative selectivity = immunoproteasome/regular proteasome. Values are normalized against that of epoxomicin Enzyme kinetics were performed by measuring the chymotrypsin-like activity of 20S immunoproteasome and regular proteasome in the presence of compound 15 using a fluorogenic peptide substrate. Although compound 15 poorly inhibited the chymotrypsin-like activity of 20S regular proteasome, it displayed a better inhibitory activity against the immunoproteasome. This is quite unusual and surprising, considering most of proteasome inhibitors inhibit the constitutive proteasome better than the immunoproteasome. More specifically, compound 15 displayed a 24-fold and 5-fold higher selectivity toward the 20S immunoproteasome in comparison to epoxomicin and dihydroeponemycin, respectively (Table 1).

Figure 6:
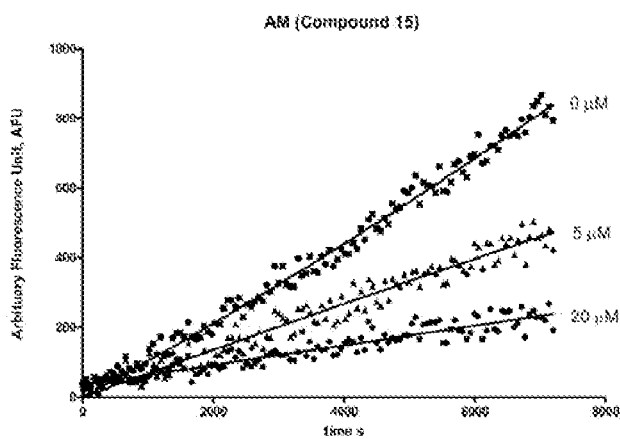
FIG. 6 is a plot showing inhibition of the immunoproteasome chymotrypsin-like activity by compound 15, in accordance with the present invention.

Referring to FIG. 6, FIG. 6 shows a time- and concentration-dependent inhibition against the chymotrypsin-like activity of 20S immunoproteasome. All together, these results provide evidence that compound 15 is a highly specific immunoproteasome inhibitor that selectively inactivates the LMP2 subunit.

In conclusion, the present epoxyketone-pharmacophore-based selective LMP2 inhibitors inhibit the catalytic function of immunoproteasome with high specificity. In addition, the LMP2 inhibitors inactivate the proteolytic activity of 20S immunoproteasome with high specificity.

The significance of the aforementioned experiments provides evidence that the present inhibitors represent a class of inhibitors which can be used as a therapeutic agent to treat diseases related to the immunoproteasome. The immunoproteasome has been implicated in a number of disease states. The immunoproteasome specific inhibitors described herein provide a therapeutic agent for hematological cancers, such as multiple myeloma, and autoimmune diseases and neurodegenerative diseases such as Alzheimer's disease and Huntington's disease, as well as provide a useful molecular probe to investigate the immunoproteasome biology.

To compare the efficacy of the present LMP2 inhibitor compounds and, in particular, LMP2 inhibitor 15, as compared to prior known inhibitors, comparative tests were conducted using compound 21 in expressing tumor cells. LMP2 inhibitor compound 21 blocked proliferation of lung cancer H460, prostate cancer cells PC3 and multiple myeloma cells RPMI8226, as summarized in Table 2, below. Western blot analysis showed that the LMP2 immunoproteasome subunit is expressed in these cell lines. Therefore, the LMP2 inhibitor compounds of the present invention, based on these results, summarized in Tables 1 and 2, provide better or superior blocking of cell proliferation in cancer cells than prior LMP2 inhibitor compounds. Thus, the present LMP2 inhibitors provide superior therapeutic agents against diseases such as myeloma, Alzheimer's disease and Huntington's disease.

TABLE 2

Cell proliferation assays were performed by counting cell numbers after 24 h incubation with compound 21, dihydroeponemycin or epoxomicin.

| | $IC_{50}$ (µM) | | | |
|---|---|---|---|---|
| Cell line | H460 (Lung) | WI-38 (Fibroblast) | PC3 (Prostate) | RPMI8226 (MM) |
| Compound 21 | 5 | 12.8 | 1.6 | 2.5 |
| Epoxomicin | 0.1 | 0.028 | 0.01 | 0.1 |

Experiments

The following experiments were conducted to demonstrate the effectiveness of the present synthesis methods for producing the dihydroeponemycin analogues. Unless otherwise stated, all reactions were carried out under nitrogen with dry freshly distilled solvents, oven-dried glassware and magnetic stirring. All solvents were reagent graded. Tetrahydrofuran (THF) was distilled from sodium/benzophenone. Methylene chloride ($CH_2Cl_2$) was distilled from calcium hydride. Diethyl ether anhydrous was purchased from EMD Chemicals and used without further purification. All reagents were purchased from Sigma-Aldrich and used without further purification. All reactions were monitored by thin layer chromatography (TLC) using E. Merk 60$F_{254}$ pre-coated silica gel plates. Flash column chromatography was performed using E. Merk silica gel 60 (particle size 0.040-0.063 mm) and with the indicated solvents. $^1$H and was recorded in $CDCl_3$ using a Varian 300 MHz spectrometer at ambient temperature using an internal deuterium lock unless stated otherwise. Chemical shift are referenced to residual chloroform (δ=7.27 ppm for $^1$H). High and low resolution mass spectra were carried out by the University of Kentucky Mass Spectrometry Facility.

Synthesis of compound 12 is described here as the representative synthetic procedure for all dihydroeponemycin analogues and, as described in "Development of the Immunoproteasome-Specific Inhibitors," Abby Ho and Kyung-Bo Kim, [Journal Name] (200_), herein incorporated by reference. Such analogues include those of formula (I).

(4S)-4-(tert-butoxycarbonyl)-amino-2-hydroxy-methyl-6-methylhept-1-en-3-one (3): Synthetic procedures were performed as previously reported in Fruh, K., Gossen, M., Wang, K., Bujard, H., Peterson, P. A., and Yang, Y. (1994), herein incorporated by reference. Displacement of housekeeping proteasome subunits by MHC-encoded LMPs: a newly discovered mechanism for modulating the multicatalytic proteinase complex. Embo. J. 13, 3236-3244.

(4S)-4-(tert-Butoxycarbonyl)-amino-2-(methoxy-ethoxymethoxymethyl)-6-methylhept-1-en-3-one (4): To a solution of compound 3 (114 mg, 0.42 mmol) in $CH_2Cl_2$ (5 ml) at 0° C. was added methoxyethoxymethyl chloride (0.24 ml, 2.1 mmol) and diisopropylethylamine (0.37 ml, 2.1 mmol). After stirring at room temperature for 3 h, the resulting mixture was pour into ice water (20 ml) and extracted with $CH_2Cl_2$ (3×20 ml). The organic layers were combined, washed with brine (20 ml), dried with $Na_2SO_4$, filtered and concentrated under reduced pressure. The product was then subjected to flash column chromatography (hexane/EtOAc, 5:1) yielding compound 4 (101 mg, 67%) as a yellowish oil. $^1$H NMR: δ=6.20 (d, $^2$J=31.8 Hz, 2H, 1-H), 5.12 (d, $^2$J=9.0 Hz, 1H, NH), 5.03 (m, 1H, 4-H), 4.75 (s, 2H, 2-$OCH_2O$), 4.28 (s, 2H, 2-$CH_2$), 3.69 (m, 2H, 2-$OCH_2CH_2O$), 3.55 (m, 2H, 2-$OCH_2CH_2O$), 3.38 (s, 3H, 2-$OCH_3$), 1.74 (m, 1H, 6-H), 1.50 (m, 1H, 5-H$^a$), 1.41 (s, 9H, $H_{BOC}$), 1.31 (m, 1H, 5-H$^b$), 0.99 (d, $^3$J=6.6 Hz, 3H, $CH_3CHCH_3$), 0.90 (d, $^3$J=6.6 Hz, 3H, $CH_3CHCH_3$) ppm.

(2RS,4S)-4-(tert-Butoxycarbonyl)-amino-2-(methoxy-ethoxymethoxymethyl)-6-methyl-1,2-oxiranyl-heptane (5, 5'): Benzonitrile (0.29 ml, 2.8 mmol), $H_2O_2$ (0.40 ml, 50% solution in $H_2O$, 7.0 mmol) and diisopropylethylamine (0.5 ml, 2.8 mmol) were added to a solution of compound 4 (100 mg, 0.28 mmol) in MeOH (5 ml) at 0° C. The reaction was stirred at 0° C. for 3 h. The resulting mixture was then concentrated under reduced pressured and subjected to flash column chromatography (hexane/EtOAc, 10:1) to yield compounds 5 and 5' with a ratio of 3:1 (60 mg, 60%). Compound 5: $^1$H NMR: δ=4.82 (d, $^2$J=8.4 Hz, 1H, NH), 4.71 (s, 2H, 2-$OCH_2O$), 4.39 (d, $^2$J=11.4 Hz, 1H, 2-$CH^a{}_2$), 4.32 (m, 1H, 4-H), 3.68 (m, 2H, 2-$OCH_2CH_2O$), 3.57 (m, 2H, 2-$OCH_2CH_2O$), 3.49 (d, $^2$J=11.4 Hz, 1H, 2-$CH^b{}_2$), 3.40 (s, 3H, 2-$OCH_3$), 3.27 (d, $^2$J=4.8 Hz, 1H, 1-H$^a$), 3.03 (d, $^2$J=4.8 Hz, 1H, 1-H$^b$), 1.75 (m, 1H, 6-H), 1.58 (m, 1H, 5-H$^a$), 1.41 (s, 9H, $H_{BOC}$), 1.13 (m, 1H, 5-H$^b$), 0.97 (d, $^3$J=6.6 Hz, 3H, $CH_3CHCH_3$), 0.94 (d, $^3$J=6.6 Hz, 3H, $CH_3CHCH_3$) ppm.

(S)—O-tert-Butyidiphenylsiloxymethyl-N-heptanoyl-serine (7): Lithium hydroxide (91 mg, 3.8 mmol) was added to a solution of (S)—O-tert-Butyldiphenyl-siloxymethyl-N-heptanoyl-seryl methyl ester (890 mg, 1.8 mmol) in methanol water (3:1) solution. Reaction was stirred at 5° C. for 15 h. Resulting mixture was poured into $H_2O$ with cold 1N HCl and extracted with $CH_2Cl_2$. The organic layers were combined, washed with brine, dried under $Na_2SO_4$, filtered, concentrated and dried under high vacuum. The product obtained yielded compound 7 as yellowish oil. $^1$H NMR: δ=7.61 (m, 4H, Ar—H), 7.41 (m, 6H, Ar—H), 6.24 (d, $^2$J=7.5 Hz, 1H, NH), 4.69 (m, 1H, 2-H), 4.17 (dd, $^2$J=10.4 Hz, $^2$J=3.6 Hz, 1H, 3-H$^a$), 3.89 (dd, $^2$J=10.4 Hz, $^2$J=3.6 Hz, 1H, 3-H$^b$), 2.20 (t, $^3$J=7.5 Hz, 2H, 2'-H), 1.60 (m, 2H, $H_{Hep}$), 1.29 (m, 6H, $H_{Hep}$), 1.05 (s, 9H, $H_{butyl}$), 0.88 (t, $^3$J=6.9 Hz, 3H, 7'-$CH_3$) ppm.

(S)—O-tert-Butyidiphenylsiloxymethyl-N-heptanoyl-seryl methyl ester: tert-Butyldiphenylsilyl chloride (1.95 ml, 7.6 mmol), imidazole (519 mg, 7.6 mmol) was added to a solution of (S)-N-heptanoyl-serine methyl ester (588.6 mg, 2.5 mmol) in $CH_2Cl_2$ (20 ml) and stirred overnight at room temperature. The resulting mixture was concentrated under reduced pressure and subjected to column chromatography (hexane/EtOAc, 5:1) yielding (S)—O-tert-Butyldiphenylsiloxymethyl-N-heptanoyl-seryl methyl ester (890 mg, 74%) as colorless oil. $^1$H NMR: δ=7.59 (m, 4H, Ar—H), 7.41 (m, 6H, Ar—H), 6.28 (d, $^2$J=8.4 Hz, 1H, NH), 4.70 (m, 1H, 2-H), 4.12 (dd, $^2$J=10.1 Hz, $^2$J=3.0 Hz, 1H, 3-H$^a$), 3.89 (dd, $^2$J=10.1 Hz, $^2$J=3.0 Hz, 1H, 3-H$^b$), 3.74 (s, 3H, 1-$OCH_3$), 2.11 (t, $^3$J=7.7 Hz, 2H, 2'-H), 1.57 (m, 2H, $H_{Hep}$), 1.30 (m, 6H, $H_{Hep}$), 1.04 (s, 9H, $H_{butyl}$), 0.88 (t, $^3$J=6.7 Hz, 3H, 7'-$CH_3$) ppm.

(S)—N-heptanoyl-serine methyl ester: To a solution of heptanoic acid (0.46 ml, 3.2 mmol) and H-Ser-$OCH_3$ (0.5 g, 3.2 mmol) in $CH_2Cl_2$ (15 ml) were added HBTU (1.83 g, 4.8 mmol), HOBt (0.74 g, 4.8 mmol) and lastly diisopropylethylamine (2.8 ml, 16 mmol). Reaction was stirred overnight at room temperature. The resulting mixture was subjected to flash column chromatography (hexane/EtOAc, 1:2) yielding (S)—N-heptanoyl-serine methyl ester (588.6 mg, 79%) as yellowish oil. $^1$H NMR: δ=6.47 (b, 1H, NH), 4.69 (m, 1H, 2-H), 3.94 (m, 2H, 3-H), 3.79 (s, 3H, 1-$OCH_3$), 2.27 (t, $^3$J=7.6 Hz, 2H, 2'-H), 1.63 (m, 2H, $H_{Hep}$), 1.29 (m, 6H, $H_{Hep}$), 0.88 (m, 3H, 7'-$CH_3$) ppm.

(4S)-2-methoxyethoxy-methoxymethyl-4-[(S)—O-tert-butyidiphenylsiloxy-methyl-N-heptanoylseryl-amino]-6-methyl-1,2-oxiranyl-heptane: Trifluoroacetic acid (100 µl, 0.87 mmol) was added to a solution of compound 5 (45 mg, 0.12 mmol) in $CH_2Cl_2$ (0.5 ml) at room temperature for 30 min. Subsequently, the concentrated mixture was dried under high vacuum to remove trifluoroacetic acid. The resulting crude product 6 (33 mg, ca. 100%) was then used in the following coupling reaction without further purification. To a solution of product 6 (33 mg, 0.12 mmol) and 7 (65 mg, 0.14 mmol) in $CH_2Cl_2$ (5 ml) were added HBTU (68 mg, 0.17 mmol), HOBt (27 mg, 0.17 mmol) and lastly diisopropylethylamine (104 µl, 0.59 mmol). Reaction was stirred overnight at room temperature. The resulting mixture was subjected to flash column chromatography (hexane/EtOAc, 3:1) to give (4S)-2-methoxyethoxy-methoxymethyl-4-[(S)—O-tert-butyldiphenylsiloxy-methyl-N-heptanoylseryl-amino]-6-methyl-1,2-oxiranyl-heptane (36 mg, 42%). $^1$H NMR: δ=7.71 (m, 4H, Ar—H), 7.44 (m, 6H, Ar—H), 7.02 (d, $^2$J=8.4 Hz, 1H, 4-NH), 6.17 (d, $^2$J=6.6 Hz, 1H, 2'-NH), 4.72 (s, 2H, 2-$OCH_2O$), 4.60 (m, 2H, 4-H, 2'-H), 4.42 (d, $^2$J=11.4 Hz, 1H, 2-$CH^a{}_2$), 4.03 (m, 1H, 3'-H$^a$), 3.70 (m, 3H, 3'-$CH^b{}_2$, 2-$OCH_2CH_2O$), 3.55 (m, 2H, 2-$OCH_2CH_2O$), 3.52 (d, $^2$J=11.4 Hz, 1H, 2-$CH^b{}_2$), 3.40 (s, 3H, 2-$OCH_3$), 3.29 (d, $^2$J=5.4 Hz, 1H, 1-H$^a$), 3.04 (d, $^2$J=4.8 Hz, 1H, 1-H$^b$), 2.13 (t, $^3$J=7.6 Hz, 2H, 2"-H), 1.63 (m, 4H, 6-H, 5-H$^a$, $H_{Hep}$), 1.26 (m, 6H, $H_{Hep}$), 1.07 (s, 9H, 3'-tBu), 0.96 (d, $^3$J=6.3 Hz, 3H, $CH_3CHCH_3$), 0.91 (d, $^3$J=6.3 Hz, 3H, $CH_3CHCH_3$), 0.86 (t, $^3$J=7.6 Hz, 3H, 7"-$CH_3$) ppm.

(4S)-2-methoxyethoxymethoxymethyl-4-N-heptanoylserylamino-6-methyl-1,2-oxiranylheptane (12): To a solution of (4S)-2-methoxyethoxy-methoxymethyl-4-[(S)—

O-tert-butyldiphenylsiloxy-methyl-N-heptanoylseryl-amino]-6-methyl-1,2-oxiranyl-heptane (30 mg, 0.042 mmol) in THF (1 ml), tetrabutylammonium fluoride (50 μl, 1 M in THF, 0.05 mmol) was added. Reaction was stirred at room temperature for 1 hour, followed by flash column chromatography (hexane/EtOAc, 1:2) yielding compound 12 (16 mg, 80%) as yellowish oil. $^1$H NMR: δ=6.83 (d, $^2$J=7.5 Hz, 1H, 4-NH), 6.44 (d, $^2$J=7.5 Hz, 1H, 2'-NH), 4.71 (s, 2H, 2-OCH$_2$O), 4.50 (m, 2H, 4-H, 2'-H), 4.41 (d, $^2$J=11.7 Hz, 1H, 2-CH$^a_2$), 4.08 (m, 1H, 3'-H$^a_2$), 3.68 (m, 2H, 2-OCH$_2$CH$_2$O), 3.55 (m, 3H, 2-OCH$_2$CH$_2$O, 3'-H$^b_2$), 3.46 (d, $^2$J=11.7 Hz, 1H, 2-CH$^b_2$), 3.40 (s, 3H, 2-OCH$_3$), 3.27 (d, $^2$J=5.1 Hz, 1H, 1-H$^a$), 3.05 (d, $^2$J=4.8 Hz, 1H, 1-H$^b$), 2.22 (m, 2H, 2"-H), 1.60 (m, 4H, 6-H, 5-H$^a$, H$_{Hep}$), 1.28 (m, 6H, H$_{Hep}$), 0.96 (d, $^3$J=3.9 Hz, 3H, CH$_3$CHCH$_3$), 0.94 (d, $^3$J=3.9 Hz, 3H, CH$_3$CHCH$_3$), 0.88 (t, $^3$J=6.7 Hz, 3H, 7"-CH$_3$) ppm. MS (ESI): m/z=475, calcd. for C$_{23}$H$_{42}$N$_2$O$_8$: m/z=474.59.

Cell Culture and Screening Assay: Murine lymphoma EL4 (ATCC) cells were grown in RPMI medium (Gibco), 10% fetal bovine serum and 1% penicillin and streptomycin at 0° C. in a 5% CO$_2$ incubator. Cells were pretreated with 1 μM biotinylated compounds 30 minutes prior to the addition of increasing concentrations of either dihydroeponemycin, epoxomicin or dihydroeponemycin analogues as indicated. The cells were then incubated for an additional 1 hour. Cell lysates were analyzed by 12% SDS-PAGE and transferred to PVDF membrane. Proteins that were covalently modified by biotinylated compounds were visualized by enhanced chemiluminescence using streptavidin conjugated horseradish peroxidase (Sigma-Aldrich) or anti-LMP2 (Affinity BioReagents) and Biomax X-ray film (Kodak).

Enzyme Kinetic Studies: $k_{association\ values}$ were determined as follows. Inhibitors were mixed with a fluorogenic peptide substrate and assay buffer [20 mM Tris (pH 8.0), 0.5 mM EDTA, and 0.035% SDS] in a 96-well plate. The chymotrypsin-like activity was assayed using the fluorogenic peptide substrates Suc-Leu-Leu-Val-Tyr-AMC (Sigma-Aldrich). Hydrolysis was initiated by the addition of bovine 20S proteasome or immunoproteasome (Biomol International), and the reaction was followed by fluorescence (360-nm excitation/460-nm detection) using a Microplate Fluorescence Reader (FL600; Bio-Tek Instruments, Inc., Winnoski, Vt.) employing the software KC4 v.2.5 (Bio-Tek Instruments, Inc., Winooski, Vt.). Reactions were allowed to proceed for 60-90 min, and fluorescence data were collected every 1 min. Fluorescence was quantified as arbitrary units and progression curves were plotted for each reaction as a function of time. $k_{observed}$/[I] values were obtained using PRISM program by nonlinear least squares fit of the data to the following equation: fluorescence=$v_s t+[(v_0-v_s)/k_{observed}][1-\exp(-k_{observed} t)]$, where $v_0$ and $v_s$ are the initial and final velocities, respectively, and $k_{observed}$ is the reaction rate constant. The range of inhibitor concentrations tested was chosen so that several half-lives could be observed during the course of the measurement. Reactions were performed using inhibitor concentrations that were <100-fold of those of the proteasome assayed.

The invention claimed is:
1. A method for synthesizing a hydroxymethyl-substituted enone, comprising the steps:
   (a) reacting Boc-Leu-OMe with dimethyl methylphosphonate treated with tert-butyllithium to form the compound,

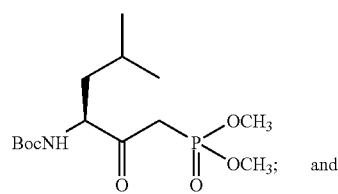

and (b) adding CH$_2$O and K$_2$O$_3$ to the product of step (a) and allowing the reagents to react to produce the hydroxymethyl-substituted enone,

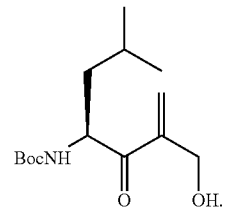

2. The method of claim 1, wherein said step (a) comprises cooling dimethyl methylphosphonate treated with tert-butyllithium in THF at −78° C. prior to adding the Boc-Leu-OMe.

3. The method of claim 1 further comprising:
   (c) adding TBDMSCl, Imidazole and CH$_2$Cl$_2$ to the hydroxymethyl-substituted enone from step (b);
   (d) adding benzonitrile, H$_2$O$_2$, i-Pr$_2$EtN and CH$_3$OH;
   (e) adding TFA and CH$_2$Cl$_2$;
   (f) adding

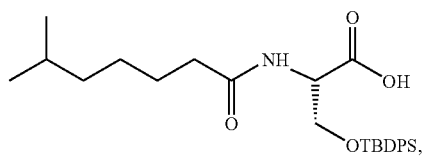

HBTU, HoBt, i-PR$_2$EtN and CH$_2$Cl$_2$, followed by TBAF and THF to produce dihydroeponemycin,

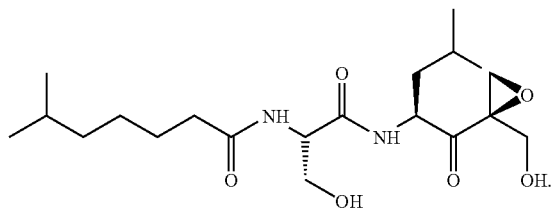

4. The method of claim 3, wherein said step (f) comprises adding

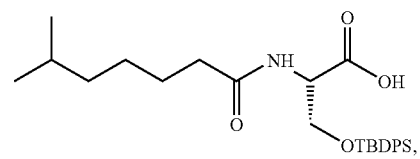

HBTU, HoBt, i-PR$_2$EtN and CH$_2$Cl$_2$ at room temperature for 12 hours before adding the TBAF and THF.

5. A P1' modified dihydroeponemycin analogue comprising a compound having the structure of formula I,

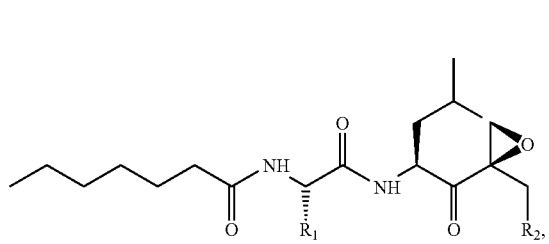

where:
R₁ is CH₃ or CH₃OH; and
R₂ is OH,

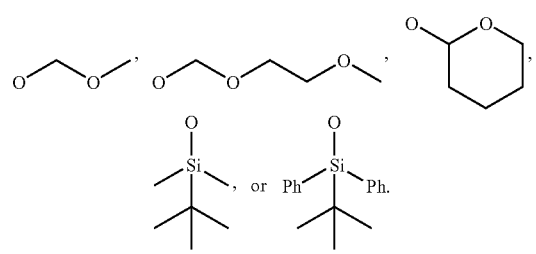

6. A method for manufacturing a P1' modified dihydroeponemycin analogue, comprising:
(a) reacting a hydroxymethyl-substituted enone,

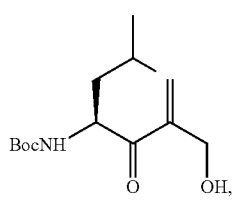

with 2-Methoxyethoxymethyl chloride, i-Pr₂EtN, CH₂Cl₂, from 0° C. to rt;
(b) adding benzonitrile, H₂O₂, i-Pr₂EtN, CH₃OH;
(c) adding TFA, CH₂Cl₂; and
(d) adding HBTU, HoBt, i-Pr₂EtN, CH₂Cl₂; and

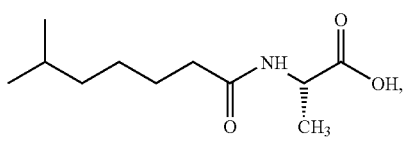

to produce P1' modified dihydroeponemycin analogue, having formula I

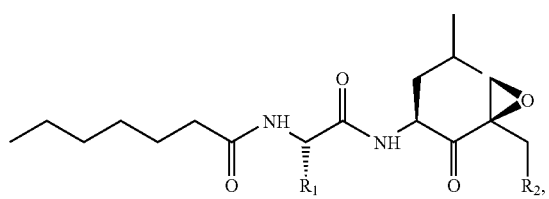

where:
R₁ is CH₃ or CH₃OH; and
R₂ is OH,

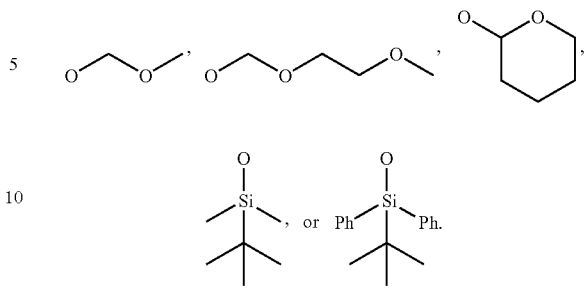

7. The method of claim 6, further comprising (e) prior to step (d), adding TBAF and THF to the product of step (c).

8. A method for treating disease by administering to a patient an effective amount of a dihydroeponemycin analogue having the formula I,

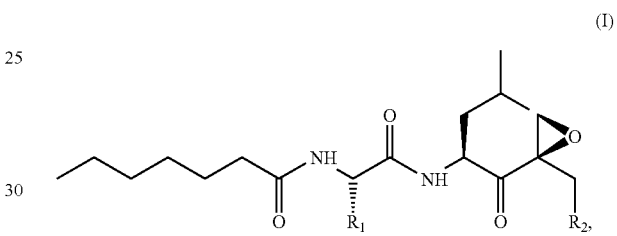

where:
R₁ is CH₃ or CH₃OH; and
R₂ is OH,

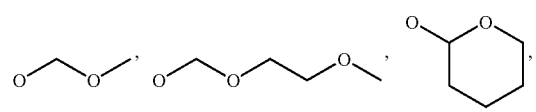

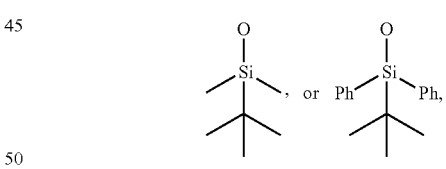

to bind to the LMP2 subunit of the immunoproteasome, thereby treating the disease.

9. The method of claim 7, wherein R₁ is CH₃ and R₂ is

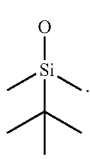

10. The method of claim 7, wherein the disease is selected from the group consisting of myeloma, Alzheimer's disease, and Huntington's disease.

11. The method of claim 9, wherein $R_1$ is $CH_3$ and $R_2$ is

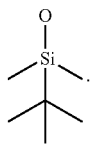

12. The method of claim 8, wherein said administering comprising administering the dihydroeponemycin analogue via intravenous administration.

13. A method of inactivating enzymatic activity of the LMP2 subunit of the immunoproteasome, comprising:
    administering to a patient in need of treatment thereof, an effective amount of a dihydroeponemycin analogue of formula I,

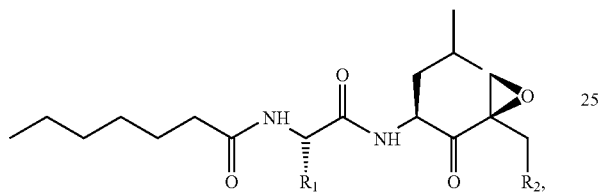
(I)

where:
  $R_1$ is $CH_3$ or $CH_3OH$; and
  $R_2$ is OH

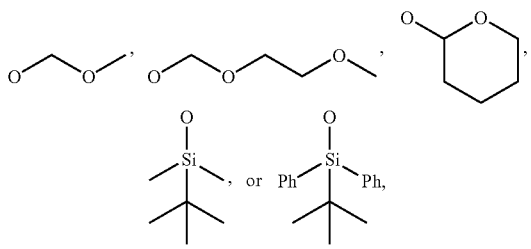

to bind to LMP2 of the immunoproteasome, to thereby inactivate the immunoproteasome.

14. The method of claim 13, wherein $R_1$ is $CH_3$ and $R_2$ is

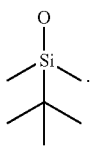

* * * * *

UNITED STATES PATENT AND TRADEMARK OFFICE
CERTIFICATE OF CORRECTION

PATENT NO. : 7,642,369 B2  
APPLICATION NO. : 11/531129  
DATED : January 5, 2010  
INVENTOR(S) : Kim et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 720 days.

Signed and Sealed this

Sixteenth Day of November, 2010

David J. Kappos  
*Director of the United States Patent and Trademark Office*